United States Patent
Gray et al.

(10) Patent No.: US 8,075,536 B2
(45) Date of Patent: Dec. 13, 2011

(54) POWER INJECTABLE PORT IDENTIFICATION

(75) Inventors: Jeff Gray, Lexington, MA (US); Marcia Buiser, Marlborough, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 0 days.

(21) Appl. No.: 12/207,205

(22) Filed: Sep. 9, 2008

(65) Prior Publication Data

US 2010/0063451 A1   Mar. 11, 2010

(51) Int. Cl.
*A61M 37/00*   (2006.01)
*A61K 9/22*   (2006.01)

(52) U.S. Cl. ......... 604/288.01; 604/288.02; 604/288.04; 604/891.1

(58) Field of Classification Search ............. 604/288.01, 604/891.1, 288.02, 288.03, 288.04
See application file for complete search history.

(56) References Cited

U.S. PATENT DOCUMENTS

| | | |
|---|---|---|
| 3,159,175 A | 12/1964 | Macmillan |
| 3,477,438 A | 11/1969 | Allen et al. |
| 3,525,357 A | 8/1970 | Koreski |
| 3,541,438 A | 11/1970 | Nelsen et al. |
| 3,669,323 A | 6/1972 | Harker et al. |
| 3,674,183 A | 7/1972 | Venable et al. |
| 3,811,466 A | 5/1974 | Ohringer |
| 3,853,127 A | 12/1974 | Spademan |
| 3,955,594 A | 5/1976 | Snow |
| 3,971,376 A | 7/1976 | Wichterle |
| 4,143,853 A | 3/1979 | Abramson |
| 4,447,237 A | 5/1984 | Frisch et al. |
| 4,543,088 A | 9/1985 | Bootman et al. |
| 4,610,665 A | 9/1986 | Matsumoto et al. |
| 4,692,146 A | 9/1987 | Hilger |
| 4,772,270 A | 9/1988 | Waiita et al. |
| 4,781,680 A | 11/1988 | Redmond et al. |
| 4,802,885 A | 2/1989 | Weeks et al. |
| 4,857,053 A | 8/1989 | Dalton |
| 4,886,501 A | 12/1989 | Johnston et al. |
| 4,886,502 A | 12/1989 | Poirier et al. |
| 4,892,518 A | 1/1990 | Cupp et al. |
| 4,897,081 A | 1/1990 | Poirier et al. |

(Continued)

FOREIGN PATENT DOCUMENTS

EP   0128525   12/1984

(Continued)

OTHER PUBLICATIONS

PCT International Search Report; International Application No. PCT/US09/05062; Nov. 3, 2009; 2 Pages.

*Primary Examiner* — Kevin C Sirmons
*Assistant Examiner* — Bradley Thomas, Jr.
(74) *Attorney, Agent, or Firm* — Bingham McCutchen LLP

(57) ABSTRACT

An implantable port for accessing internal body structures, the port comprises a proximal housing including an opening providing access to an interior of the port and a distal housing adapted for assembly with the proximal housing, the distal housing including a reservoir which, when the distal housing is mated with the proximal housing is in fluid communication with the opening of the proximal housing in combination with a radiopaque element in one of the proximal and distal housings, a shape of the radiopaque element identifying, when imaged, a structural characteristic of the port not otherwise identifiable visually.

19 Claims, 5 Drawing Sheets

U.S. PATENT DOCUMENTS

| | | | |
|---|---|---|---|
| 4,904,241 A | 2/1990 | Bark | |
| 4,908,029 A | 3/1990 | Bark et al. | |
| 4,929,236 A | 5/1990 | Sampson | |
| 5,009,391 A | 4/1991 | Steigerwald | |
| 5,009,644 A | 4/1991 | McDonald | |
| 5,045,060 A | 9/1991 | Melsky et al. | |
| 5,053,013 A | 10/1991 | Ensminger et al. | |
| 5,059,186 A | 10/1991 | Yamamoto et al. | |
| 5,069,206 A | 12/1991 | Crosbie | |
| 5,084,015 A | 1/1992 | Moriuchi | |
| 5,092,849 A | 3/1992 | Sampson | |
| 5,129,891 A | 7/1992 | Young | |
| 5,137,529 A | 8/1992 | Watson et al. | |
| 5,147,483 A | 9/1992 | Melsky et al. | |
| 5,167,638 A | 12/1992 | Felix et al. | |
| 5,180,365 A | 1/1993 | Ensminger et al. | |
| 5,205,834 A | 4/1993 | Moorehead et al. | |
| 5,242,415 A | 9/1993 | Kantrowitz et al. | |
| 5,249,598 A | 10/1993 | Schmidt | |
| 5,263,930 A | 11/1993 | Ensminger | |
| 5,281,199 A | 1/1994 | Ensminger et al. | |
| 5,312,337 A | 5/1994 | Flaherty et al. | |
| 5,318,545 A | 6/1994 | Tucker | |
| 5,350,360 A | 9/1994 | Ensminger et al. | |
| 5,352,204 A | 10/1994 | Ensminger | |
| 5,356,381 A | 10/1994 | Ensminger et al. | |
| 5,387,192 A | 2/1995 | Glantz et al. | |
| 5,396,925 A | 3/1995 | Poli et al. | |
| 5,399,168 A | 3/1995 | Wadsworth, Jr. et al. | |
| 5,417,656 A | 5/1995 | Ensminger et al. | |
| 5,423,334 A | 6/1995 | Jordan | |
| 5,453,097 A | 9/1995 | Paradis | |
| 5,476,451 A | 12/1995 | Ensminger et al. | |
| 5,520,643 A | 5/1996 | Ensminger et al. | |
| 5,527,277 A | 6/1996 | Ensminger et al. | |
| 5,527,278 A | 6/1996 | Ensminger et al. | |
| 5,531,684 A | 7/1996 | Ensminger et al. | |
| 5,542,923 A | 8/1996 | Ensminger et al. | |
| 5,554,117 A | 9/1996 | Ensminger et al. | |
| 5,556,381 A | 9/1996 | Ensminger et al. | |
| 5,558,641 A | 9/1996 | Glantz et al. | |
| 5,562,618 A | 10/1996 | Cai et al. | |
| 5,607,393 A | 3/1997 | Ensminger et al. | |
| 5,613,945 A | 3/1997 | Cai et al. | |
| RE35,601 E | 9/1997 | Eckenhoff | |
| 5,662,616 A | 9/1997 | Bousquet | |
| 5,707,357 A | 1/1998 | Mikhail et al. | |
| 5,741,228 A | 4/1998 | Lambrecht et al. | |
| 5,755,780 A | 5/1998 | Finch et al. | |
| 5,792,104 A | 8/1998 | Speckman et al. | |
| 5,792,123 A | 8/1998 | Ensminger | |
| 5,797,886 A | 8/1998 | Roth et al. | |
| 5,814,016 A | 9/1998 | Valley et al. | |
| 5,848,989 A | 12/1998 | Villani | |
| 5,879,322 A | 3/1999 | Lattin et al. | |
| 5,882,341 A | 3/1999 | Bousquet | |
| 5,897,528 A | 4/1999 | Schultz | |
| 5,906,596 A | 5/1999 | Tallarida | |
| 5,911,706 A | 6/1999 | Estabrook et al. | |
| 5,941,856 A | 8/1999 | Kovacs et al. | |
| 5,944,688 A | 8/1999 | Lois | |
| 5,944,698 A | 8/1999 | Fischer et al. | |
| 5,954,687 A | 9/1999 | Baudino | |
| 5,954,691 A | 9/1999 | Prosl | |
| 5,961,497 A | 10/1999 | Larkin | |
| 5,989,216 A | 11/1999 | Johnson et al. | |
| 6,056,717 A | 5/2000 | Finch et al. | |
| 6,086,555 A | 7/2000 | Eliasen et al. | |
| 6,099,508 A | 8/2000 | Bousquet | |
| 6,152,909 A | 11/2000 | Bagaoisan et al. | |
| 6,210,366 B1 | 4/2001 | Sanfilippo | |
| 6,287,293 B1 * | 9/2001 | Jones et al. | 604/891.1 |
| 6,306,124 B1 | 10/2001 | Jones et al. | |
| 6,527,754 B1 | 3/2003 | Tallarida et al. | |
| 6,592,571 B1 | 7/2003 | Verbeek et al. | |
| 6,610,031 B1 | 8/2003 | Chin | |
| 6,726,063 B2 | 4/2004 | Stull et al. | |
| 6,962,577 B2 | 11/2005 | Tallarida et al. | |
| 7,033,339 B1 | 4/2006 | Lynn | |
| 2001/0016717 A1 | 8/2001 | Haarala et al. | |
| 2001/0056266 A1 | 12/2001 | Tallarida et al. | |
| 2002/0013557 A1 | 1/2002 | Sherry | |
| 2002/0121530 A1 | 9/2002 | Socier | |
| 2003/0109856 A1 | 6/2003 | Sherry | |
| 2003/0141477 A1 | 7/2003 | Miller | |
| 2003/0216694 A1 | 11/2003 | Tollini | |
| 2004/0133173 A1 | 7/2004 | Edoga et al. | |
| 2004/0186444 A1 | 9/2004 | Daly et al. | |
| 2005/0010176 A1 | 1/2005 | Dikeman et al. | |
| 2005/0027234 A1 | 2/2005 | Waggoner et al. | |
| 2005/0027261 A1 | 2/2005 | Weaver et al. | |
| 2005/0080401 A1 | 4/2005 | Peavey | |
| 2006/0178647 A1 * | 8/2006 | Stats | 604/288.01 |
| 2006/0224129 A1 | 10/2006 | Beasley et al. | |
| 2006/0247584 A1 | 11/2006 | Sheetz et al. | |
| 2007/0078391 A1 | 4/2007 | Wortley et al. | |
| 2007/0100302 A1 | 5/2007 | DiCarlo et al. | |
| 2007/0233017 A1 * | 10/2007 | Zinn et al. | 604/288.01 |

FOREIGN PATENT DOCUMENTS

| | | |
|---|---|---|
| EP | 0343910 | 11/1989 |
| EP | 0366814 | 5/1990 |
| FR | 2508008 | 12/1982 |
| FR | 2809315 | 11/2001 |
| GB | 0966137 | 8/1964 |
| GB | 2102398 | 2/1983 |
| WO | WO-92/06732 | 4/1992 |
| WO | WO-94/05351 | 3/1994 |
| WO | WO-95/16480 | 6/1995 |
| WO | WO-97/01370 | 1/1997 |
| WO | WO-97/23255 | 7/1997 |
| WO | WO-97/26931 | 7/1997 |
| WO | WO-98/18506 | 8/1997 |
| WO | WO-00/12171 | 3/2000 |
| WO | WO-00/16844 | 3/2000 |
| WO | WO-00/33901 | 6/2000 |
| WO | WO-01/60444 | 8/2001 |
| WO | WO-03/084832 | 10/2003 |
| WO | WO-2005/068009 | 7/2005 |

\* cited by examiner

POWER INJECTABLE PORT IDENTIFICATION

BACKGROUND

Implantable ports are designed for patients who require long term access to the central venous system or other internal structures for the administration and/or withdrawal of fluids, including hydration fluids, antibiotics, chemotherapy, analgesics, nutritional therapy and blood products. A catheter is typically inserted to form a path to the vascular system by advancing a distal end of the catheter into a blood vessel while a proximal end is connected to the port that is implanted subcutaneously. The port is generally placed under the skin on the upper part of the chest wall or the upper arm, and allows patients to access the desired body lumen while avoiding repeated needlesticks to the target structure. Power injectable implantable ports offer the additional advantage of providing access for the power injection of contrast agents to enhance imaging, such as Contrast-Enhanced Computer Tomography (CECT) scans, which rely on intravenously administered contrast agents to enhance the visibility of internal structures. The contrast agent is power injected into the blood stream to highlight features that would otherwise be difficult to distinguish from nearby tissues. Thus, power injectable ports provide access for the standard injection and withdrawal of fluids (e.g., for therapeutic purposes) and for power injection of contrast agents to enhance imaging.

Although, it is desirable to use ports which are also suitable for power injection, users must be able to positively identify such ports to ensure they are not accessing a port which is not useable for power injection. The industry has established a "CT" mark, which when viewed under a CT scan, is a standard indication of power injectability. Some existing "CT" identifying technologies known in the field today include a cut-through "CT" design through the port body. The limitation of this design is the space available on the port that would allow for adequate size and visibility of the "CT" lettering. Another disadvantage of cut-through design is that the space could promote tissue ingrowth, which may make it more difficult to remove the port later.

Pad printing the "CT" letters onto the port using radiopaque ink is another existing technology. Radiopaque ink prevents X-rays or similar radiation waves to pass therethrough so that they may be identified in scans. However, the radiopaque ink in these ports is often located on an outer surface of the port, which can be susceptible to damage such as smearing, cracking and fragmenting in the subcutaneous environment, making the marking unreadable. In addition, fragments of ink may migrate, leading to ink integrity issues.

Another CT identifying technology is used in the POWERPORT®, manufactured by Bard Access Systems Inc., Salt Lake City, Utah. The POWERPORT® includes an external metal component with "CT" lettering at the base. However, the "CT" lettering occupies a space on the base of the port where the device labeling is typically placed. Device labeling may include manufacturer and/or lot numbers, which may be helpful in identifying the port. In addition, there is a risk of the external component becoming separated from the device.

SUMMARY OF THE INVENTION

The present invention is directed to an implantable port for accessing internal body structures, the port comprises a proximal housing including an opening providing access to an interior of the port and a distal housing adapted for assembly with the proximal housing, the distal housing including a reservoir which, when the distal housing is mated with the proximal housing is in fluid communication with the opening of the proximal housing in combination with a radiopaque element in one of the proximal and distal housings, a shape of the radiopaque element identifying, when imaged, a structural characteristic of the port not otherwise identifiable visually.

DETAILED DESCRIPTION

Figure 1:
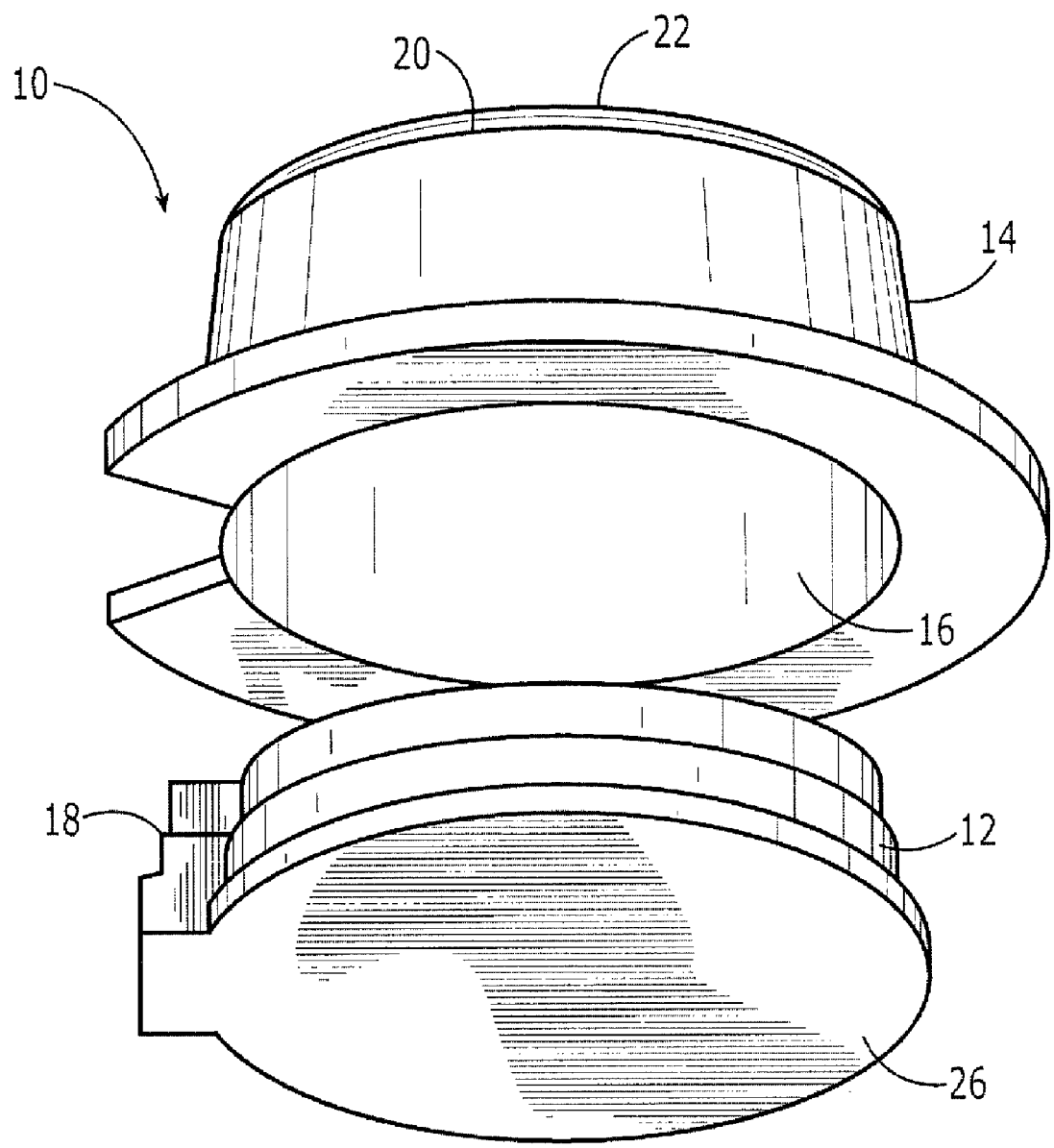
FIG. 1 shows a port according to an exemplary embodiment the invention.

The present invention may be further understood with reference to the following description of exemplary embodiments and the related appended drawings, wherein like elements are provided with the same reference numerals. The present invention relates to devices for accessing the vascular system via a catheter and, more specifically, relates to a power-injectable port that may be identified as such after implantation. Those skilled in the art will understand that the ports described herein are generally implanted with an opening through which fluids are to be introduced or withdrawn facing the skin. As used in this application, the term proximal refers to a direction toward the skin while distal refers to a distance deeper into the body.

Figure 2:
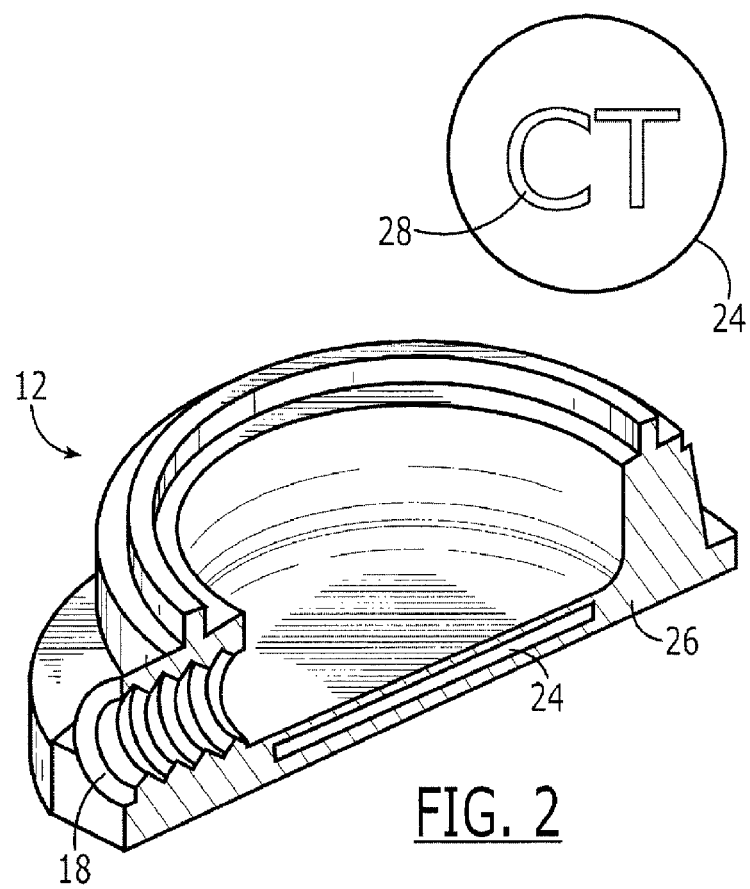
FIG. 2 shows a cross-sectional view of a distal housing of the port of FIG. 1.

As shown in FIGS. 1 and 2, a port 10 according to an exemplary embodiment the invention comprises a distal housing 12 and a proximal housing 14 which are mated together to seal an internal reservoir 16 coupled to a fluid outlet 18 which is coupled to a body structure to which fluids are to be supplied and/or from which fluids are to be withdrawn. A proximal surface of the proximal housing 14 includes an opening 20 via which fluids are supplied and/or withdrawn from the reservoir 16. The opening 20 is sealed by a self-sealing septum 22. Thus, the reservoir and the body structure to which the outlet 18 is coupled may be accessed by passing a needle through the septum 22 with the septum 22 resealing itself as soon as the needle is withdrawn, as would be understood by those skilled in the art.

As shown in FIG. 2, a radiopaque insert 24 is embedded in a base 26 of the distal housing 12. The radiopaque insert 24 incorporates an identifying mark 28 (e.g., a CT mark or other indication of characteristics of the port) visible through the use of one or more types of electromagnetic scan such as X-rays, etc. As would be understood by those skilled in the art, the radiopaque insert 24 may be formed of any material having the desired radiopaque properties (e.g., titanium). The identifying mark 28 may, for example, be cut-through the radiopaque insert 24 allowing the scanning radiation to pass therethrough in a pattern indicative of a characteristic (e.g., suitability for power injection) of the port 10. Those skilled in the art will understand that, as the insert 24 is embedded in the distal housing 12, the cut-through design of the identifying mark 28 will be clearly visible without increasing the likelihood of tissue ingrowth. The CT mark shown in FIG. 2 is for illustrative purposes only, and it will be understood by those of skill in the art that a CT mark on the radiopaque insert 24 may be a mirror image of the marking shown so that the CT may be legible when viewed under the electromagnetic scan.

As would be understood by those skilled in the art, the radiopaque insert 24 may be embedded within distal housing 12 via an insert molding process in which the radiopaque insert 24 is robotically or hand loaded into a mold cavity between shots. The insert 24 is supported in position in the mold by a series of needle-like core pins and, during injection, these pins are retracted into the mold base as the plastic fills the cavity and encapsulates the insert. Once the insert 24 has been embedded in the distal housing 12, the distal housing 12 is ready to be assembled with the other port components in the same manner for a port without such a radiopaque insert 24. Standard assembly techniques such as ultrasonic welding, snap fit or solvent bond may be utilized as would be understood by those skilled in the art.

Figure 3:
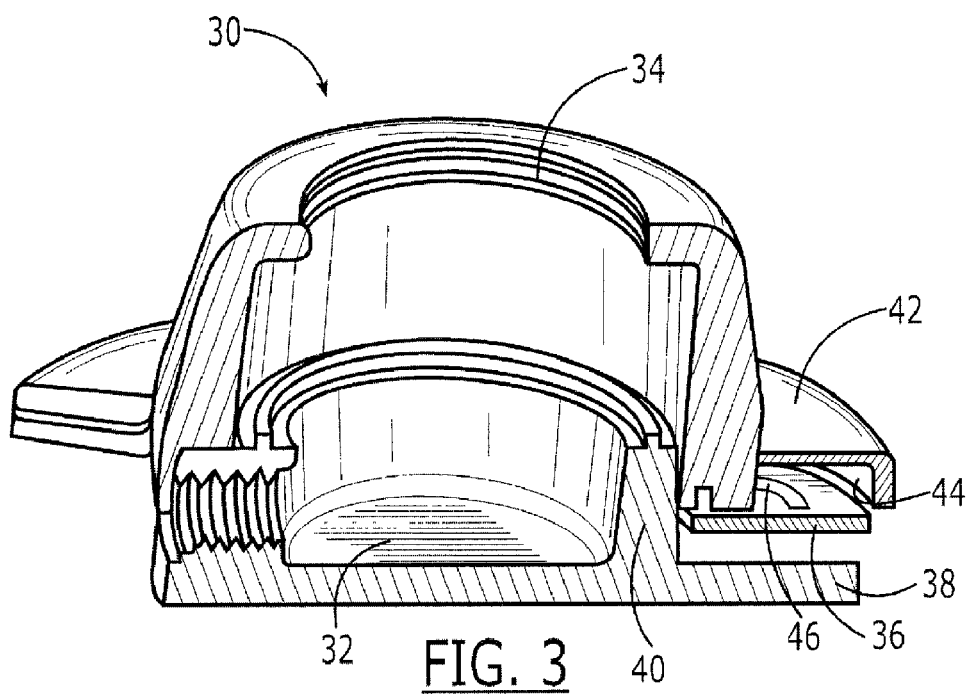
FIG. 3 shows a cross-sectional view of a port according to another embodiment of the invention.
Figure 4:
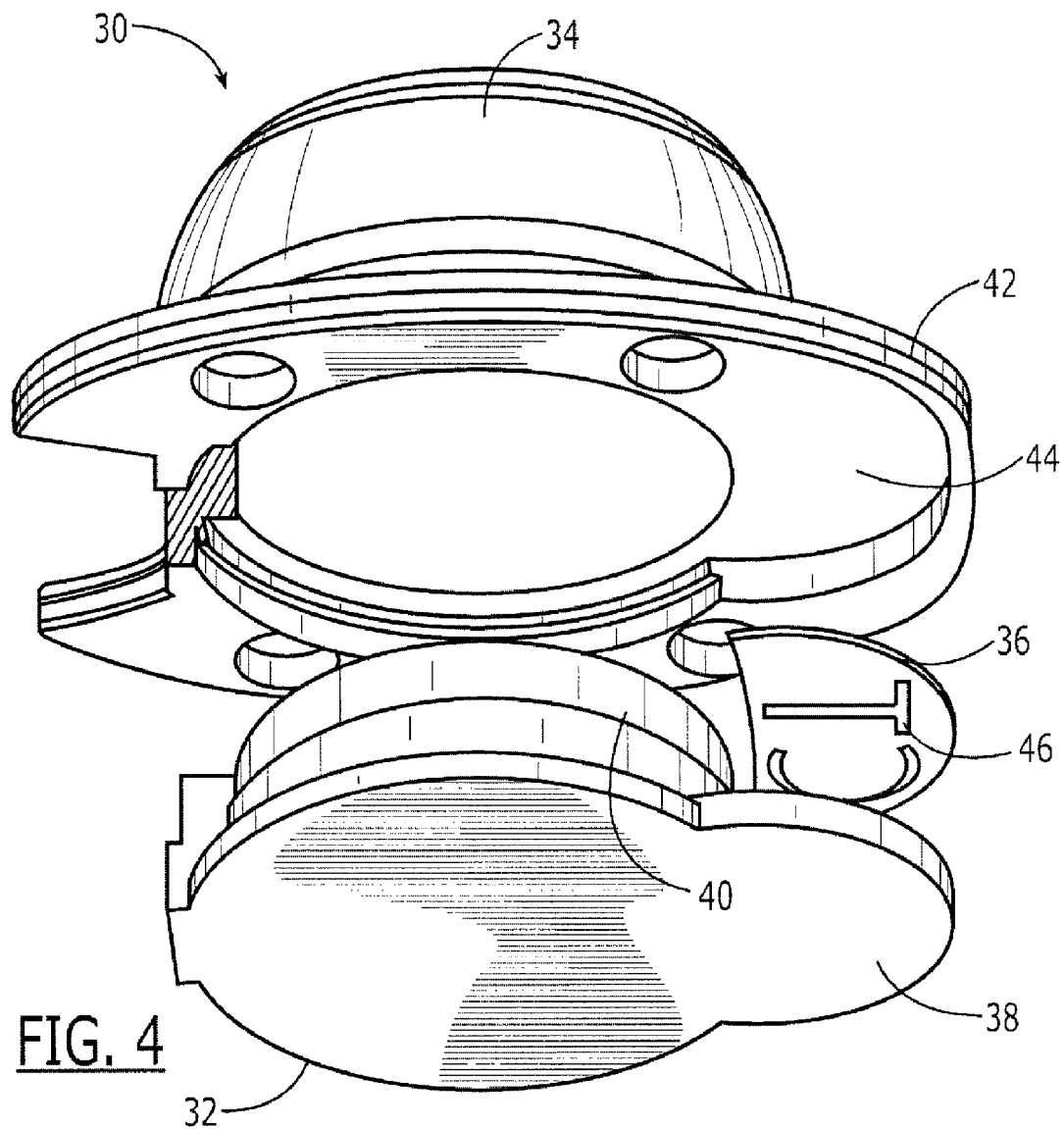
FIG. 4 shows an exploded view of the port of FIG. 3.

As shown in FIGS. 3 and 4, a port 30 according to another embodiment of the invention comprises a distal housing 32, a proximal housing 34 and a radiopaque insert 36. The distal housing 32 includes a distal flange 38 extending radially outward from a wall of 40 of the distal housing forming a reservoir of the port 30 with a corresponding proximal flange 42 of the proximal housing 34 extending thereover when assembled with the distal housing 32. The proximal housing 34 is preferably formed so that, when mated with the distal housing 32, a recess 44 is formed between the distal and proximal flanges 38, 42, respectively. The radiopaque insert 36 is received in the recess 44 between the distal and proximal flanges 38, 42, respectively. The distal housing 32 and the proximal housing 34 may then be joined via any standard plastic joining process, such as ultrasonic welding, snap-fit, and solvent bond, to hold the radiopaque insert 36 in place as would be understood by those skilled in the art.

As described above, the radiopaque insert 36 may be made of any radiopaque material with an identifying mark 46 (e.g., CT) cut-out so that the mark 46 is clearly visible when imaged using any of the known scanning techniques. As the insert 36 is housed between the proximal and distal flanges 38, 42, respectively, the cut-out poses no risk of tissue ingrowth and the risk of the insert 36 becoming detached from the port 30 is also minimized.

In a further embodiment of the present invention, the radiopaque insert 36 may be embedded in either of the proximal and distal flanges 38, 42, respectively using an insert molding process. As described above, the radiopaque insert 36 may be placed into a mold cavity between shots and held in place by a series of needle-like core pins. During injection, these pins are retracted into the mold base as plastic fills the cavity and encapsulates the insert 36. Once the insert 36 has been embedded, the distal housing 32 is ready to be assembled with the other port components including the proximal housing 34 as described above.

Figure 5:
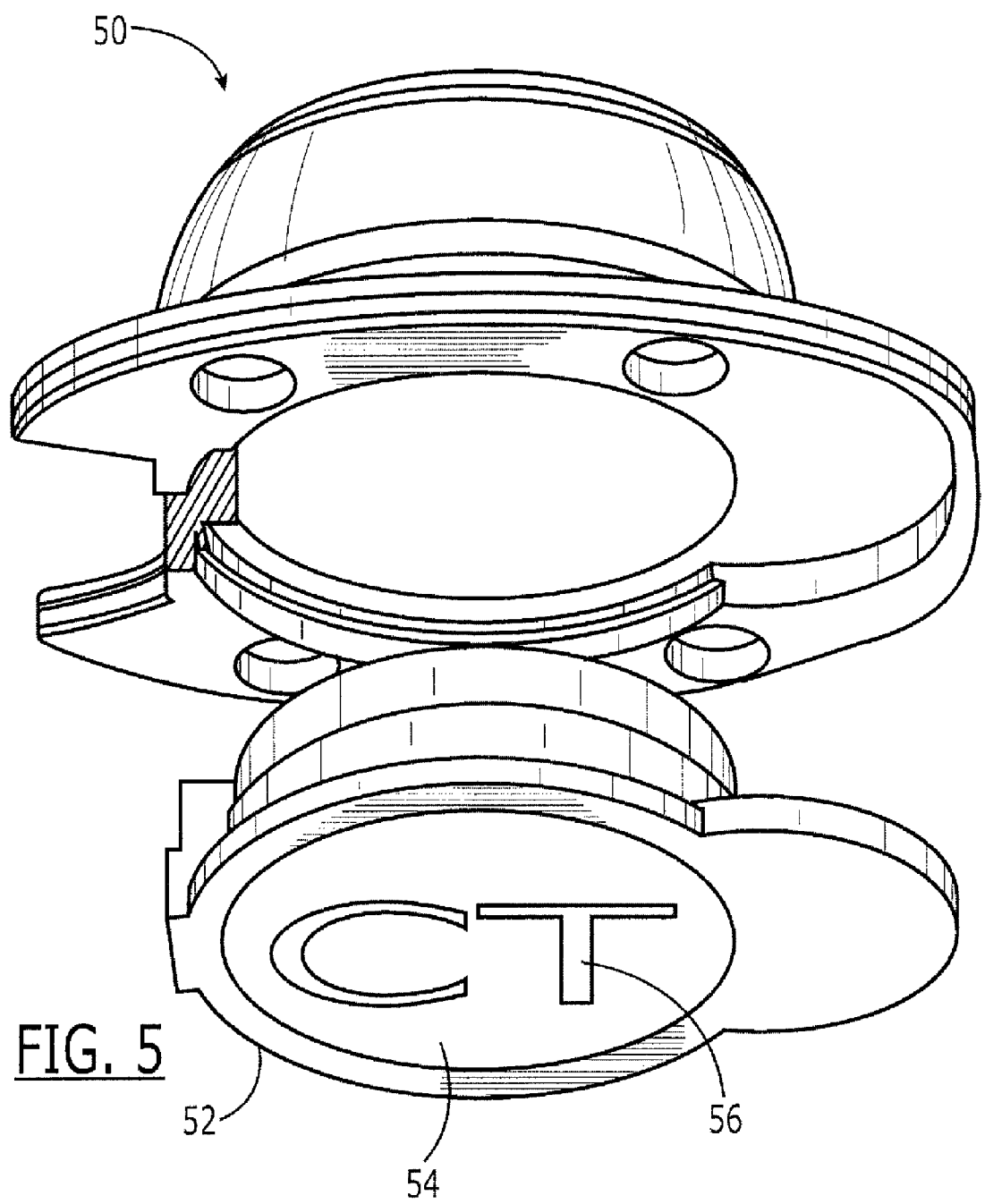
FIG. 5 shows an exploded bottom view of a port according to another embodiment of the invention.

In another embodiment of the present invention, as shown in FIG. 5, a port 50 comprises a distal housing 52 and a radiopaque insert 54 having a periphery shaped to define an identifying mark 56. Those skilled in the art will understand that, when the identifying mark consists of more than one element (e.g., multiple letters) a minimal amount of radiopaque material may extend between these elements to maintain a desired alignment during the molding process. The insert 54 may be overmolded into the distal housing 52 by inserting it into the cavity before injection. The plastic would form around the insert, leaving the surface of the CT mark visible on the underside of the base. The distal housing 52 with overmolded radiopaque insert 54 may be assembled with the rest of the port components using any standard assembly techniques as described above.

In a further embodiment, the overmolded insert 54 may be mechanically combined with a port stem and inserted into the mold. Overmolding would then encapsulate and seal the insert 54 into the distal housing 52 while simultaneously binding the stem to the distal housing 52. Such an embodiment provides a radiopaque marker for power injectability while eliminating a separate stem/port assembly step.

Figure 6:
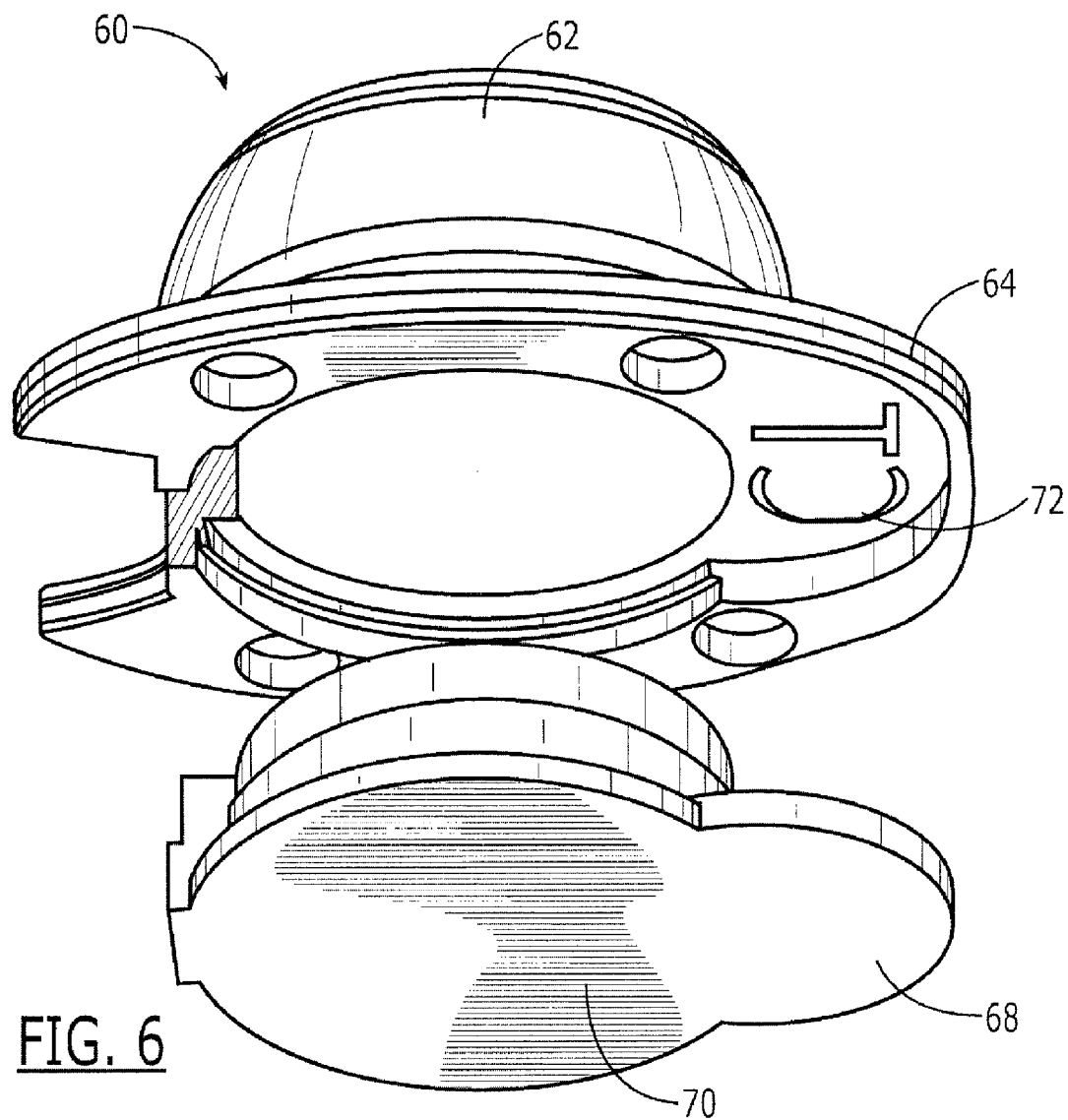
FIG. 6 shows an exploded view of a port according to yet another embodiment of the invention.

In another embodiment of the present invention, shown in FIG. 6, a port 60 comprises a proximal housing 62 that may be molded using plastic loaded with radiopaque fillers such as barium, bismuth, and tungsten. The proximal housing 62 includes a proximal flange 64 extending radially outward therefrom with a corresponding distal flange 68 extending radially outward from a distal housing 70 in the same manner described above in regard to the port 30 of FIGS. 3 and 4. The proximal flange 64 includes an identifying mark 72 mark cut through a thickness thereof (e.g., during a molding process). The distal housing 70, or at least the distal flange 68, is formed of standard plastic with no radiopaque fillers so that the mark 72 creates a "negative" of the mark 72 when imaged (e.g., under CT or other body scan). In order to prevent tissue ingrowth, a silicone boot or skirt may be incorporated such that the boot or skirt covers the cut-through lettering. It will be understood by those of skill in the art that the boot or skirt may additionally be composed of any suitable non-radiopaque material. Furthermore, those skilled in the art will understand that the distal housing 70 may, alternatively, be formed of a material incorporating radiopaque fillers with the mark 72 cut out of the distal flange 68 while the proximal housing 64 is formed of a material free of radiopaque fillers.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. An implantable port for accessing internal body structures, the port comprising:
   a proximal housing including an opening providing access to an interior of the port;
   a distal housing adapted for assembly with the proximal housing, the distal housing including a reservoir which, when the distal housing is mated with the proximal housing is in fluid communication with the opening of the proximal housing, wherein the distal housing includes a first flange extending radially outward from a wall thereof forming the reservoir and wherein the proximal housing includes a second flange extending radially outward and corresponding to the first flange, the second flange being sized to cover the first flange when the distal and proximal housings are mated with one another to form the port, and wherein the first and second flanges are formed so that, when the distal and proximal housings are mated with one another to form the port, a recess is formed between a proximal surface of the first flange and a distal surface of the second flange and wherein a radiopaque element is received in the recess; and
   the radiopaque element in one of the proximal and distal housings, the radiopaque element identifying, when imaged, a characteristic of the port not otherwise visually identifiable after implantation within a living body.

2. The port of claim 1, wherein one of the first and second flanges is formed of a material including a radiopaque filler and the other of the first and second flanges is formed of a material transparent to an imaging radiation and wherein the one of the first and second flanges formed of a material including a radiopaque filler includes a cut-out shaped to identify the structural characteristic of the port.

3. The port of claim 2, wherein the one of the first and second flanges formed of a material including a radiopaque filler includes a covering member to prevent tissue ingrowth into the cut-out.

4. The port of claim 1, wherein the radiopaque element is molded into the first flange.

5. The port of claim 1, wherein the radiopaque element is molded into a portion of the distal housing forming a distal wall of the reservoir.

6. The port of claim 5, wherein the radiopaque element is overmolded on the distal housing so that the radiopaque element is visible as a part of a distal surface of the port.

7. The port of claim 6, wherein a periphery of the radiopaque element is shaped to identify the structural characteristic of the port.

8. The port of claim 6, wherein an interior cut-out of the radiopaque element is shaped to identify the structural characteristic of the port.

9. The port of claim 1, wherein the radiopaque element includes a cut-through.

10. The port of claim 9, wherein the cut-through indicates that the port is suitable for power injection.

11. The port of claim 10, wherein the cut-through is in the shape of CT.

12. The port of claim 1, wherein the radiopaque element is embedded in one of the proximal and distal housings.

13. The port of claim 12, wherein the radiopaque element is embedded using an insert molding process.

14. The port of claim 13, wherein the radiopaque element is embedded in the distal housing.

15. The port of claim 12, wherein an outlet stem of the port is overmolded to one of the proximal and distal housings when the radiopaque element is embedded.

16. The port of claim 1, wherein the radiopaque element is overmolded into the distal housing such that identifying information of the radiopaque element is visible on a bottom surface of the distal housing.

17. The port of claim 16, wherein the radiopaque element is coupled to an outlet stem prior to being overmolded into the distal housing.

18. The port of claim 1, wherein the distal housing is assembled with the proximal housing using one of an ultrasonic welding process, a snap fit mechanism, and a solvent bond.

19. The port of claim 1, wherein the radiopaque element includes titanium.

* * * * *